(12) United States Patent
Felkner

(10) Patent No.: US 6,346,201 B1
(45) Date of Patent: Feb. 12, 2002

(54) OZONATED SOLUTIONS OF TETRASILVER TETROXIDE

(75) Inventor: I. Cecil Felkner, Columbia, MD (US)

(73) Assignee: ICF Technologies, Inc., New City, NY (US)

(*) Notice: Subject to any disclaimer, the term of this patent is extended or adjusted under 35 U.S.C. 154(b) by 0 days.

(21) Appl. No.: 09/543,140

(22) Filed: Apr. 5, 2000

(51) Int. Cl.⁷ .................................................. C02F 1/78
(52) U.S. Cl. ........................ 210/760; 210/764; 252/175; 252/186.1; 422/28; 423/604
(58) Field of Search ................................. 210/760, 764; 252/175, 186.1, 186.21; 422/28; 423/604

(56) References Cited

U.S. PATENT DOCUMENTS

| | | |
|---|---|---|
| 4,176,061 A | 11/1979 | Stopka |
| 4,517,159 A | 5/1985 | Karlson |
| 4,608,247 A | 8/1986 | Heinig, Jr. |
| 5,017,295 A | 5/1991 | Antelman |
| 5,073,382 A | 12/1991 | Antelman |
| 5,078,902 A | 1/1992 | Antelman |
| 5,089,275 A | 2/1992 | Antelman |
| 5,098,582 A | 3/1992 | Antelman |
| 5,211,855 A | 5/1993 | Antelman |
| 5,223,149 A | 6/1993 | Antelman |
| 5,336,416 A | 8/1994 | Antelman |
| 5,336,499 A | 8/1994 | Antelman |
| 5,352,369 A | 10/1994 | Heinig, Jr. |
| 5,709,546 A | 1/1998 | Waggoner |
| 5,772,896 A | 6/1998 | Denkewicz, Jr. et al. |

OTHER PUBLICATIONS

Antelman, "Silver (II, III) Disinfectants," Soap/Cosmetics/Chemical Specialties, Mar. 1994, pp. 52–59.
Derwent Abstract of JP 54062198 (May 18, 1979).

*Primary Examiner*—Betsy Morrison Hoey
(74) *Attorney, Agent, or Firm*—Caesar, Rivise, Bernstein, Cohen & Pokotilow, Ltd.

(57) ABSTRACT

The invention provides an ozonated form of the compound tetrasilver tetroxide, a water disinfection method employing the ozonated tetrasilver tetroxide and compositions comprising the ozonated tetrasilver tetroxide. Examples of compositions of the invention include beverages, sterilants and disinfectants. In addition, the invention provides a method for increasing a half-life of ozone in water, where the method includes providing tetrasilver tetroxide in the water along with the ozone.

21 Claims, 3 Drawing Sheets

OZONATED SOLUTIONS OF TETRASILVER TETROXIDE

FIELD OF THE INVENTION

This invention relates to compositions containing multivalent silver compounds that have been exposed to ozone, and more particularly to aqueous solutions containing ozone-activated tetrasilver tetroxide.

BACKGROUND OF THE INVENTION

It is conventionally understood that water, particularly standing bodies of water, can be an effective breeding ground or reservoir for a variety of undesirable microbes. Thus, a wide variety of water treatment systems have been developed to disinfect potable water and/or maintain it at a safe level.

Perhaps the most common disinfection method for drinking or recreational water is chlorination. However, it has been found that chlorine has an objectionable odor, and can cause skin irritations and serious eye irritations to users of recreational bodies of water, such as pools, spas, etc. More importantly, chlorine forms trihalomethanes in the presence of organic materials and these compounds present a potential health threat due to their carcinogenicity and mutagenicity. Because of the long term health threat and objectionable physical properties of chlorine, a number of alternate water treatment systems that operate without chlorine have been developed in recent years.

Another gas used to disinfect water is ozone. According to U.S. Pat. No. 4,176,061 to Stopka, the ability of ozone to purify drinking water has been appreciated for some time. Stopka cites a number of references that teach the advantages of using ozone rather than chlorine to decontaminate water. What Stopka does not disclose is that ozone, like chlorine, has some disadvantages. Perhaps most significant of these disadvantages is that ozone, as a gas, can dissipate from water over time, leaving the water once again susceptible to contamination by various pathogens.

A number of water disinfection systems rely on the oligodynamic effect provided by the addition to water of, e.g., transition metals such as silver.

For example, U.S. Pat. No. 4,608,247 to Heinig, Jr. discloses water treatment systems comprising exposing the water to a material which erodes to provide particulate silver in the water. Although the particulate silver is said to be ionic, and the patent does not disclose the valency of the ions formed by erosion, other references, such as Antelman, "Silver (II, III) Disinfectants," Soap/Cosmetics/Chemical Specialties, pp. 52–59 (March 1994) at page 52, third paragraph, suggest that trace ions formed from silver metal are monovalent.

U.S. Pat. No. 5,352,369 to Heinig, Jr. acknowledges that water treatment systems like that disclosed in Heinig's earlier '247 patent are only partially effective in avoiding the use of chlorine as an antimicrobial agent, in that such systems often require the addition of reduced amounts of chlorine to water treated by such systems. The '369 patent purports to avoid this limitation on prior silver-based systems, in providing a method of treating water by generating an active oxidizer in the water which is capable of attacking and killing a wide range of microorganisms therein. The method comprises exposing the water to a silver catalyst in the presence of oxygen to form an active oxidizer in the water and, in some instances to also release silver ions (presumably monovalent silver ions as discussed above) therein via an erosion process similar to that set forth in Heinig's '247 patent. The silver catalyst utilized in the method comprises an alumina matrix having between approximately 0.1% and 5% by weight of elemental silver chemically deposited thereon. The oxygen utilized in the method preferably also comprises ozone.

U.S. Pat. Nos. 5,017,295, 5,073,382, 5,078,902, 5,089,275, 5,098,582, 5,211,855 and 5,223,149 to Antelman disclose water treatment methods comprising adding multivalent silver compounds to water.

U.S. Pat. No. 5,211,855 to Antelman discloses and claims a water treatment method comprising adding tetrasilver tetroxide to water bodies, such as reservoirs. At column 1, Antelman discloses that his previous patents were incorrect in identifying the antimicrobial agent as silver (II) oxide (i.e., AgO), when it is actually tetrasilver tetroxide (i.e., $Ag_4O_4$), wherein each molecule comprises one pair of monovalent silver atoms and one pair of trivalent silver atoms.

U.S. Pat. No. 5,223,149 to Antelman discloses the use of trivalent silver compounds as bactericidal and algicidal agents in water treatment. Antelman asserts that these trivalent silver compounds are an improvement over his earlier divalent silver compounds, which are disclosed and claimed in his earlier U.S. patents identified above. Antelman at the paragraph bridging columns 1–2 teaches that oxidizing agents are not required to be used with the trivalent silver compounds.

Despite the foregoing developments, there is still room in the art for improved water treatment systems.

All references cited herein are incorporated herein by reference in their entireties.

SUMMARY OF THE INVENTION

The invention provides an ozonated form of the compound tetrasilver tetroxide, a water disinfection method employing the ozonated tetrasilver tetroxide and compositions comprising the ozonated tetrasilver tetroxide. Examples of compositions of the invention include beverages and disinfectants.

In addition, the invention provides a method for increasing the half-life of ozone in water, said method comprising providing tetrasilver tetroxide in the water along with the ozone.

BRIEF DESCRIPTION OF THE DRAWINGS

The invention will be described in conjunction with the following drawings in which like reference numerals designate like elements and wherein.

DETAILED DESCRIPTION OF PREFERRED EMBODIMENTS

Figure 1:
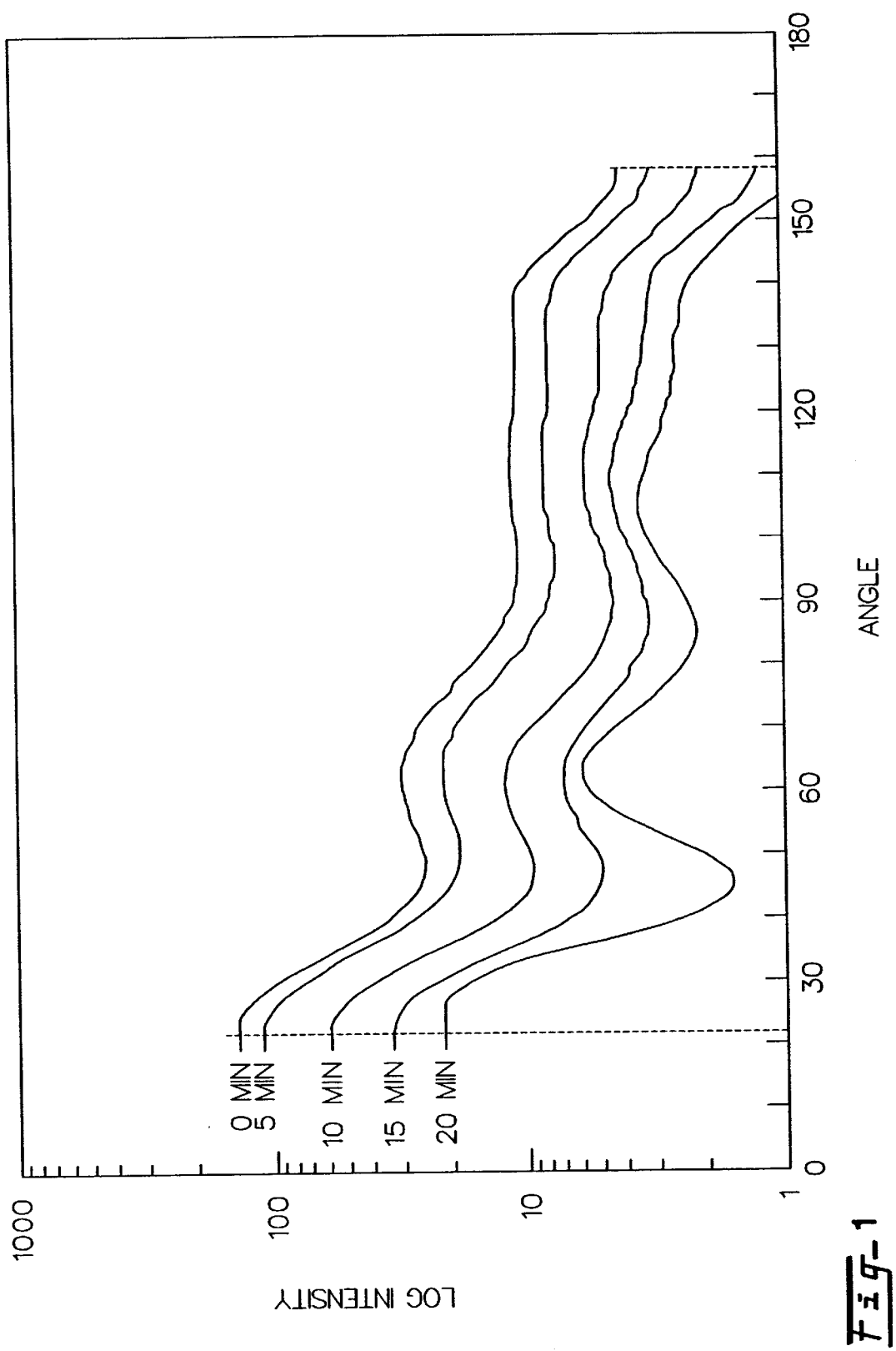
FIGS. 1, 2 and 3 are Multiple Angle Light Scattering (MALS) graphs of log intensity vs. angle.

The inventor has discovered that the ozonated form of the compound tetrasilver tetroxide has an antimicrobial effect greater than that of non-oxidated tetrasilver tetroxide. Prior to the inventor's discovery, it was known that potassium monopersulfate could activate the antimicrobial effect of tetrasilver tetroxide, but the inventor is unaware of any suggestion in the prior art that ozone is also capable of activating this effect. In embodiments of the invention, ozonated tetrasilver tetroxide has an antimicrobial effect at least equal to that of potassium monopersulfate-activated tetrasilver tetroxide. Moreover, activating tetrasilver tetroxide with ozone avoids the drawbacks of using potentially hazardous and/or toxic chemicals as activation agents.

Although there has been some confusion in the art regarding the precise nature of tetrasilver tetroxide, U.S. Pat. No. 5,211,855 describes tetrasilver tetroxide as a molecule, $Ag_4O_4$, having one pair of monovalent silver atoms and one pair of trivalent silver atoms. While not necessarily wishing to be bound by this theory in its entirety, the term "tetrasilver tetroxide" as used herein is intended to identify the compound $Ag_4O_4$.

Tetrasilver tetroxide is the most preferred oligodynamic compound of the invention; however, it is contemplated that the other oligodynamic compounds, such as trivalent silver (see, e.g., U.S. Pat. No. 5,223,149 to Antelman), multivalent copper (see, e.g., U.S. Pat. No. 5,336,416 to Antelman), and other multivalent heavy metal compounds, can be substituted for tetrasilver tetroxide in certain embodiments of the invention.

Tetrasilver tetroxide is ozonated by a process comprising providing non-activated tetrasilver tetroxide and ozone in a fluid medium. The medium can be ozonated before, during and/or after addition of tetrasilver tetroxide thereto. Water is the preferred fluid medium, but other liquid or gaseous media in which ozone can be solubilized can be suitable for use in the invention, e.g., various peroxides, ethers, alcohols or acids, such as peracetic acid.

The initial ratio of ozone to tetrasilver tetroxide provided in the medium is preferably 1:10 to 10:1, more preferably at least 1:2, most preferably at least 1;1. The amount of ozone is preferably from 0.5 to 7.0 ppm, and more preferably from 4 to 6 ppm. The concentration of non-activated tetrasilver tetroxide is preferably from 0.5 to 7.0 ppm, and more preferably from 2 to 6 ppm. Greater amounts of either ingredient might be wasteful or cause undesirable side effects. Lesser amounts of either ingredient might not be sufficiently microcidal to achieve a desired antimicrobial effect.

Although it is preferred to initially provide ozone in the above-identified concentrations, such concentrations need not be maintained throughout the life of the resulting composition. In embodiments, ozone is actively removed or passively dissipates from the composition over time, yielding a composition substantially devoid of ozone in which ozone-activated tetrasilver tetroxide continues to function as an antimicrobial agent.

In view of the heretofore unknown ability of ozone to activate tetrasilver tetroxide, it is not necessary to provide other activating agents in the composition, such as potassium monopersulfate.

Compositions of the invention are suitable for a wide variety of purposes. For example, the compositions can be consumed as beverages (e.g., as bottled water, municipal tap water, etc.) or can be applied as cleaning agents to substrates in need of cleaning (i.e., disinfection, etc.). The concentration of tetrasilver tetroxide and/or ozone may be adjusted according to the intended use. For example, the concentration of at least one ingredient might be raised above the preferred concentrations mentioned above to prepare a disinfectant composition unsuitable for human consumption. Of course, such a composition would preferably be packaged in a container labeled as a cleaning product so as to avoid accidental human consumption.

Water disinfection is the most preferred use for ozonated tetrasilver tetroxide of the invention. Water disinfection according to the invention can be as simple as providing ozonated tetrasilver tetroxide in water. This can be done in accordance with the methods described above for providing ozonated tetrasilver tetroxide compositions. The water decontaminated can be used for consumption (e.g., via municipal water distribution systems), recreation (e.g., in pools), manufacturing (e.g., as a raw material, solvent, etc.), etc.

The water disinfection method of the invention enjoys several advantages over conventional water treatment methods employing ozone without tetrasilver tetroxide or tetrasilver tetroxide without ozone. In addition to the unexpected activation of tetrasilver tetroxide by ozone described above, tetrasilver tetroxide has an unexpected effect on ozone. The inventor has discovered that the half-life of ozone in water is increased by tetrasilver tetroxide. As the dissipation of ozone from treated water over time and distance has posed a major limitation on the use of ozone in municipal water treatment, the ability of tetrasilver tetroxide to extend the half-life of ozone in water is a very significant advantage of the invention.

The combined effects of ozone and tetrasilver tetroxide also facilitate the use of lesser amounts of at least one of the two ingredients relative to prior art methods using only one of the two ingredients. This can improve the quality of the product of the method (e.g., by minimizing the undesirable odor of ozone), while decreasing production costs.

Embodiments of the invention are useful to kill pathogens, including but not limited to: vegetative bacteria and spores, such as Clostridium or Bacillus species; viruses; protozoans; and protozoan cysts and oocysts, such as Giardia and Cryptosporidium. Non-pathogenic simulants, such as *Bacillus subtilis* and *Bacillus stearothermophilus* spores, are used to demonstrate the efficacy of treatment because they are more resistant to disinfection than any known water-borne pathogens.

The invention will be illustrated in more detail with reference to the following Examples, but it should be understood that the present invention is not deemed to be limited thereto.

Comparative Examples

Efficacy of Tetrasilver Tetroxide on *E. coli* K12 Culture

*E. coli* has long been recognized for its association with fecal contamination of water and the presence of many enteric pathogens. A sample of *E. coli* K12 strain was grown on TSA (tryptic soy agar) at 37° C. for 24 hours for use as a test organism. The following measurements were obtained after 24 hours:

Acridine Orange Direct Count: $1.05 \times 10^8$ cells/mL;

Plate Count on TSA: $3.95 \times 10^8$ cells/mL;

Stock Culture Plate Count: $2.27 \times 10^8$ cells/mL; and 1 hour culture in water: $2.71 \times 10^7$ cells/mL (untreated control).

The efficacy of tetrasilver tetroxide (SILDATE, N. Jonas & Co., Bensalem, Pa.) in the absence of ozone was evaluated by performing TSA plate counts on *E. coli* K12 strain samples having the following additives:

(A) 1 ppm tetrasilver tetroxide+10 ppm potassium monopersulfate (PMP);

(B) 2 ppm tetrasilver tetroxide+20 ppm of PMP;

(C) 5 ppm tetrasilver tetroxide+50 ppm of PMP; and (D) 10 ppm tetrasilver tetroxide+100 ppm of PMP.

PMP is a compound known to activate the antimicrobial effect of tetrasilver tetroxide. The counts were taken at various time intervals. The results are tabulated in Table 1.

TABLE 1

TSA plate counts (*E. coli* K12 survival)

Plate Count (cells/mL) over Time (in minutes)

| Additive | 5 | 10 | 20 | 30 | 60 |
|---|---|---|---|---|---|
| A | — | — | — | $5.1 \times 10^3$ | 0 |
| B | — | $1.5 \times 10^6$ | 0 | — | — |
| C | $2.5 \times 10^6$ | 0 | — | — | — |
| D | 0 | — | — | — | — |

It was observed that 10 ppm tetrasilver tetroxide activated with 100 ppm PMP kills 100% of the test pathogen at five minutes or less. Other studies have indicated that 10 ppm or less tetrasilver tetroxide kills 100% of *E. coli* K12 strain within 30 minutes. Tetrasilver tetroxide (5 ppm) activated with 50 ppm PMP kills 90% in 5 minutes and 100% in 10 minutes. Tetrasilver tetroxide (2 ppm) activated with 20 ppm PMP kills 95% in 10 minutes and 100% in 20 minutes. Tetrasilver tetroxide (1 ppm) activated with 10 ppm PMP kills 4 logs in 30 minutes and 100% in 1 hour.

Efficacy of Ozone

The efficacy of ozone in the absence of tetrasilver tetroxide was evaluated by challenging *Bacillus subtilis* spores with 2 ppm ozone and measuring the survival rate over time by MALS, acridine orange direct counts (AODC) and by counting colony forming units (CFU) at 24 hours. The results are tabulated in Table 2. The resulting MALS graphs are shown in FIG. 1.

FIG. 1 shows a reduction in the log intensity as a direct function of increasing time of exposure to ozone, thus demonstrating the killing effect of ozone in water. Similar results were obtained using a spore suspension of *B. stearothermophilus*. Water suspensions of bacterial spores were chosen because they are the most resistant form of microbes known, even more resistant than oocysts of Cryptosporidium and cysts of Giardia, neither of which is inactivated by chlorine.

Ozone is, of course, effective against enteric pathogens. For example, adding 3.2 ppm $O_3$ to a test culture kills $1.95 \times 10^6$ cells/mL of *E. coli* in 1 minute and kills $1.5 \times 10^6$ cells/mL of *P. aeruginosa* in 1 minute.

EXAMPLE 1

Ozone-Activated Tetrasilver Tetroxide with Ozone Removed

An ozone generator was used to study the effects of ozonated tetrasilver tetroxide (OTT) on *E. coli* K12 Survival. The ozone generator for all of the examples was a Model CD-1B generator supplied by AQUA-FLO, Inc., 6244 Frankford Ave., Baltimore, Md. 21206. Ozone was generated from oxygen supplied from a tank with oxygen purity of more than 99.9%. The generator was fitted with a voltage regulator and an oxygen flow regulator which enabled the oxygen flow/voltage parameters to be precisely set so that the desired concentration of ozone could be maintained continuously or a given level attained and allowed to revert back to oxygen based on its half-life. When oxygen flowed through the generator, high voltage converted it to ozone, which was bubbled into water. Excess (head) ozone passed through a platinum catalyst that converted it back to oxygen.

By use of toggle switches, the ozone was directed through glass spargers into either of two specially designed 2-liter Erlenmeyer flasks containing 1 liter of water. Either a solution of a test chemical or a suspension of microorganisms or both could be introduced into the flasks via tubes at the top which passed through a rubber stopper (which seals off the system). Samples could be withdrawn at the bottom of the flask by opening a stopcock.

Ozone concentrations were measured by a chemical oxidation of indigo dye by using an indigo dye calorimeter manufactured by HACH, Inc.

Water containing 6 ppm tetrasilver tetroxide was ozonated with 3 ppm ozone for 15 minutes, followed by 40 minutes of vigorous aeration to remove ozone from the water. The ozone concentration was measured by a HACH POCKET COLORIMETER using ACCUVAC ampules by the indigo dye oxidation method. The initial ozone concentration of 3.0 mg/L (i.e:, 3 ppm) was reduced to 0.09 mg/L after 40 minutes of aeration and was further reduced to undetectable levels before the ozone-activated tetrasilver tetroxide solution was used to challenge *E. coli* K12.

*E. coli* overnight cultures were challenged with either 3.0 or 6.0 ppm of ozone-activated (i.e., ozonated) tetrasilver tetroxide and plated onto TSA after each exposure time. The results are tabulated in Table 3.

TABLE 2

| Treatment | MALS | | AODC | | 24-Hour Count | | |
|---|---|---|---|---|---|---|---|
| Time | intensity | % control | spores/mL | % control | cfu/mL | % control | % AODC |
| 0 | 2436.6 | 100 | $2.34 \times 10^6$ | 100 | $2.10 \times 10^6$ | 100 | 100 |
| 5 | 1591.92 | 65.33 | $1.6 \times 10^6$ | 68.3 | $1.23 \times 10^6$ | 58.5 | 76.9 |
| 10 | 1264.26 | 51.89 | $1.16 \times 10^6$ | 49.5 | $1.68 \times 10^5$ | 8.0 | 14.5 |
| 15 | 1039.64 | 42.67 | $1.29 \times 10^6$ | 55.1 | $1.80 \times 10^3$ | 0.09 | 0.14 |
| 20 | 851.5 | 34.94 | $4.87 \times 10^5$ | 20.8 | $1.82 \times 10^2$ | 0.009 | 0.04 |
| 30 | 681.2 | 27.96 | $5.03 \times 10^5$ | 21.5 | 10 | 0.00005 | 0.002 |

TABLE 3

Survival of *E. coli* K12 following treatment with ozone-activated tetrasilver tetroxide

| OTT Concentration (ppm) | Exposure Time (min) | Count (cfu/mL) | Percent Survival |
|---|---|---|---|
| 0 | 0 | $2.14 \times 10^6$ | 100 |
| 3 | 5 | $4.5 \times 10^6$ | 100 |
| 3 | 10 | $1.59 \times 10^6$ | 76 |
| 3 | 15 | $3.6 \times 10^5$ | 17.2 |
| 3 | 20 | $8.1 \times 10^4$ | 3.9 |

TABLE 3-continued

Survival of *E. coli* K12 following treatment
with ozone-activated tetrasilver tetroxide

| OTT Concentration (ppm) | Exposure Time (min) | Count (cfu/mL) | Percent Survival |
|---|---|---|---|
| 3 | 30 | 0 | 0 |
| 6 | 5 | $1.77 \times 10^6$ | 85.2 |
| 6 | 10 | $8.8 \times 10^4$ | 4.2 |
| 6 | 15 | $1.7 \times 10^2$ | 0.08 |
| 6 | 20 | 0 | 0 |
| 6 | 30 | 0 | 0 |

This example demonstrates that the antimicrobial effect of tetrasilver tetroxide can be activated by ozone, and persists after separation of the ozone from the tetrasilver tetroxide.

EXAMPLE 2

Ozone-Activated Tetrasilver Tetroxide and 0.03 ppm Ozone 6 ppm tetrasilver tetroxide was ozonated in water at an ozone concentration of 5.7 ppm for 16 minutes and aerated vigorously for 30 minutes to provide a final ozone level of 0.03 ppm. An *E. coli* K12 overnight culture (22 hours) was then treated with 0, 1, 2 or 6 ppm of the activated tetrasilver tetroxide for 0, 10, 20 or 30 min. The results are tabulated in Table 4.

TABLE 4

Effect of ozone-activated tetrasilver
tetroxide on *E. coli* K12 with varying times
of exposure

| OTT Concentration (ppm) | Exposure Time (min) | Count (cfu/mL) | Percent Survival |
|---|---|---|---|
| 6 | 10 | 0 | 0 |
| 6 | 20 | 0 | 0 |
| 6 | 30 | 0 | 0 |
| 2 | 10 | $1.1 \times 10^4$ | 2.3 |
| 2 | 20 | 0 | 0 |
| 2 | 30 | 0 | 0 |
| 1 | 10 | $1.7 \times 10^5$ | 36 |
| 1 | 20 | $1.02 \times 10^4$ | 2 |
| 1 | 30 | 55–100 | <0.02 |
| 0 | 0 | $4.7 \times 10^5$ | 100 |
| 0 | 60 | $3.6 \times 10^5$ | 76 |

EXAMPLE 3

Ozone-Activated Tetrasilver Tetroxide and 0.04 ppm Ozone 6 ppm of tetrasilver tetroxide was ozonated at an ozone concentration of 6.6 ppm for 16 min in water and vigorously aerated for 30 minutes to provide a final ozone concentration of 0.04 ppm. An *E. coli* K12 overnight culture (22 hours) was then treated with 1 or 2 ppm of the activated tetrasilver tetroxide for 0, 10, 20 or 30 min. The results are tabulated in Table 5.

TABLE 5

Effect of ozone-activated tetrasilver
tetroxide on *E. coli* K12 with varying times
of exposure

| OTT Concentration (ppm) | Exposure Time (min) | Count (cfu/mL) | Percent Survival |
|---|---|---|---|
| 2 | 10 | $1.02 \times 10^6$ | 27 |
| 2 | 20 | $1.47 \times 10^4$ | 0.7 |
| 2 | 30 | $1.25 \times 10^2$ | 0.02 |
| 1 | 10 | $3.2 \times 10^6$ | 85 |
| 1 | 20 | $2.21 \times 10^6$ | 58 |
| 1 | 30 | $1.14 \times 10^4$ | 1 |
| 0 | 10 | $3.75 \times 10^6$ | 100 |
| 0 | 20 | $2.12 \times 10^6$ | 57 |
| 0 | 30 | $1.05 \times 10^6$ | 28 |
| 0 (No $O_3$) | 0 | $6.5 \times 10^6$ | — |
| 0 (No $O_3$) | 45 | $6.4 \times 10^6$ | — |

EXAMPLE 4

2 ppm Tetrasilver Tetroxide and 0.32 ppm Ozone

Figure 2:
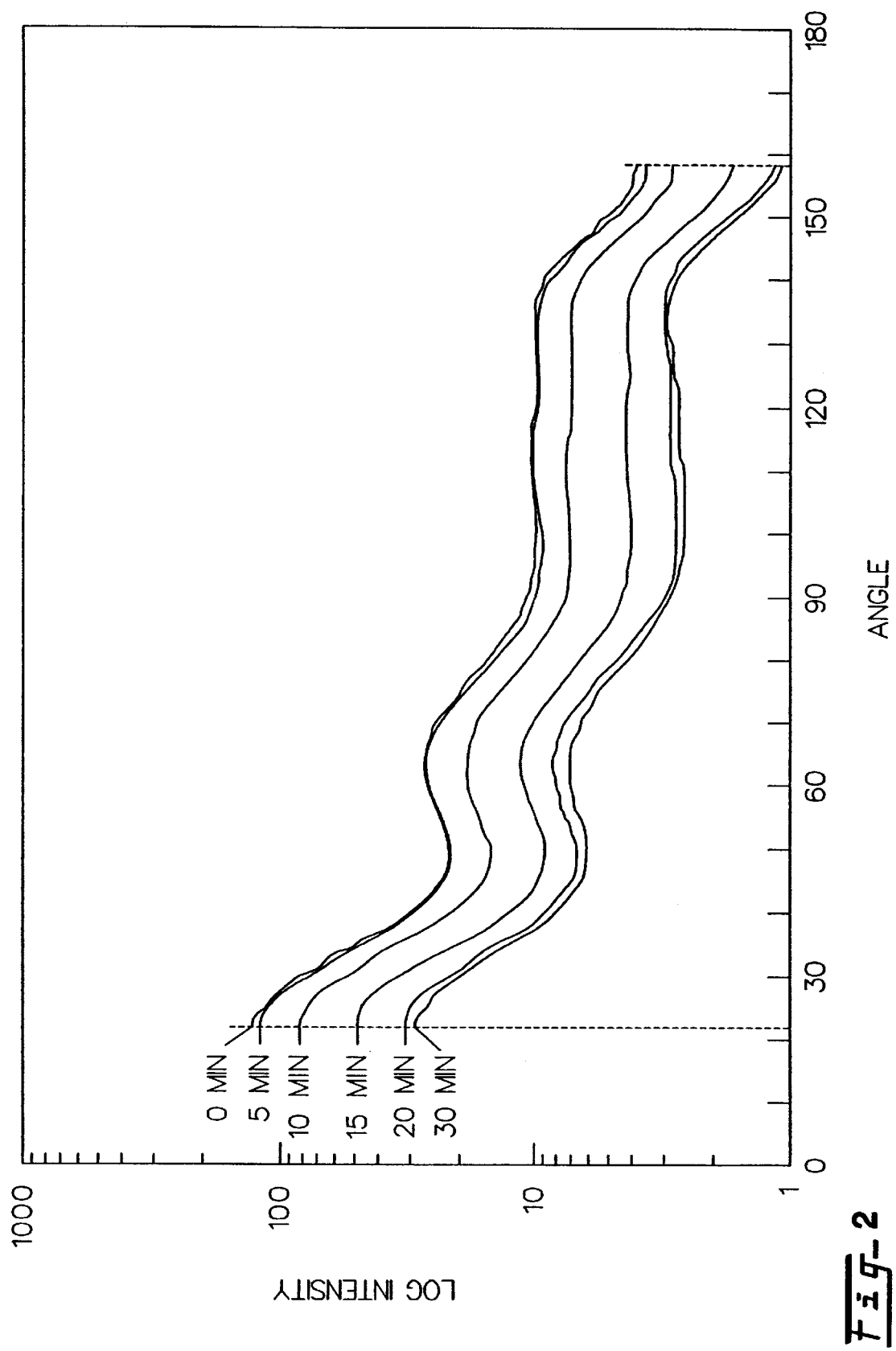

*Bacillus subtilus* spore suspensions in water were challenged with 2 ppm tetrasilver tetroxide and 0.3 2 ppm ozone to evaluate the killing efficacy of the combination. The survival rate over time was measured by MALS, AODC and counting colony forming units at 24 hours. The results are tabulated in Table 6. The resulting MALS graphs are shown in FIG. 2.

TABLE 6

Effect of ozone (0.32 ppm) and tetrasilver tetroxide (2 ppm)
on spores of *B. subtilis* at varying times of treatment

| Treatment Time | MALS | | AODC | | 24-Hour Count (cfu) | | |
|---|---|---|---|---|---|---|---|
| | intensity | % control | spores/mL | % control | cfu/mL | % control* | % AODC |
| 0 | 1754.33 | 100 | $2.07 \times 10^6$ | 100 | $1.47 \times 10^6$ | 91 | — |
| 5 | 1754.33 | 78.3 | $2.05 \times 10^6$ | 88.7 | $1.38 \times 10^6$ | 85 | 67.3 |
| 10 | 1203.75 | 53.0 | $1.19 \times 10^6$ | 57.5 | $2.38 \times 10^5$ | 14 | 0.20 |
| 15 | 724.2 | 32.0 | $5.36 \times 10^5$ | 25.9 | $7.14 \times 10^2$ | 0.6 | 0.13 |
| 20 | 508.08 | 22.7 | $2.81 \times 10^5$ | 13.3 | $0.95 \times 10^2$ | 0.005 | 0.03 |

TABLE 6-continued

Effect of ozone (0.32 ppm) and tetrasilver tetroxide (2 ppm)
on spores of *B. subtilis* at varying times of treatment

| Treatment Time | MALS intensity | % control | AODC spores/mL | % control | 24-Hour Count (cfu) cfu/mL | % control* | % AODC |
|---|---|---|---|---|---|---|---|
| 25 | 443.68 | 19.8 | $2.18 \times 10^5$ | 10.3 | $0.30 \times 10^2$ | 0.002 | 0.016 |
| 30 | 485.86 | 21.7 | $1.90 \times 10^5$ | 9.0 | $0.35 \times 10^2$ | 0.002 | 0.018 |
| 35 | 502.86 | 22.4 | $2.31 \times 10^5$ | 10.9 | $0.20 \times 10^2$ | 0.001 | 0.087 |

*Control cfu was $1.62 \times 10^6$ cfu/ml

FIG. 2 shows a reduction in the log intensity as function of increasing time of exposure to ozone and tetrasilver tetroxide, thus demonstrating the antimicrobial effect of ozonated tetrasilver tetroxide in water.

Figure 3:
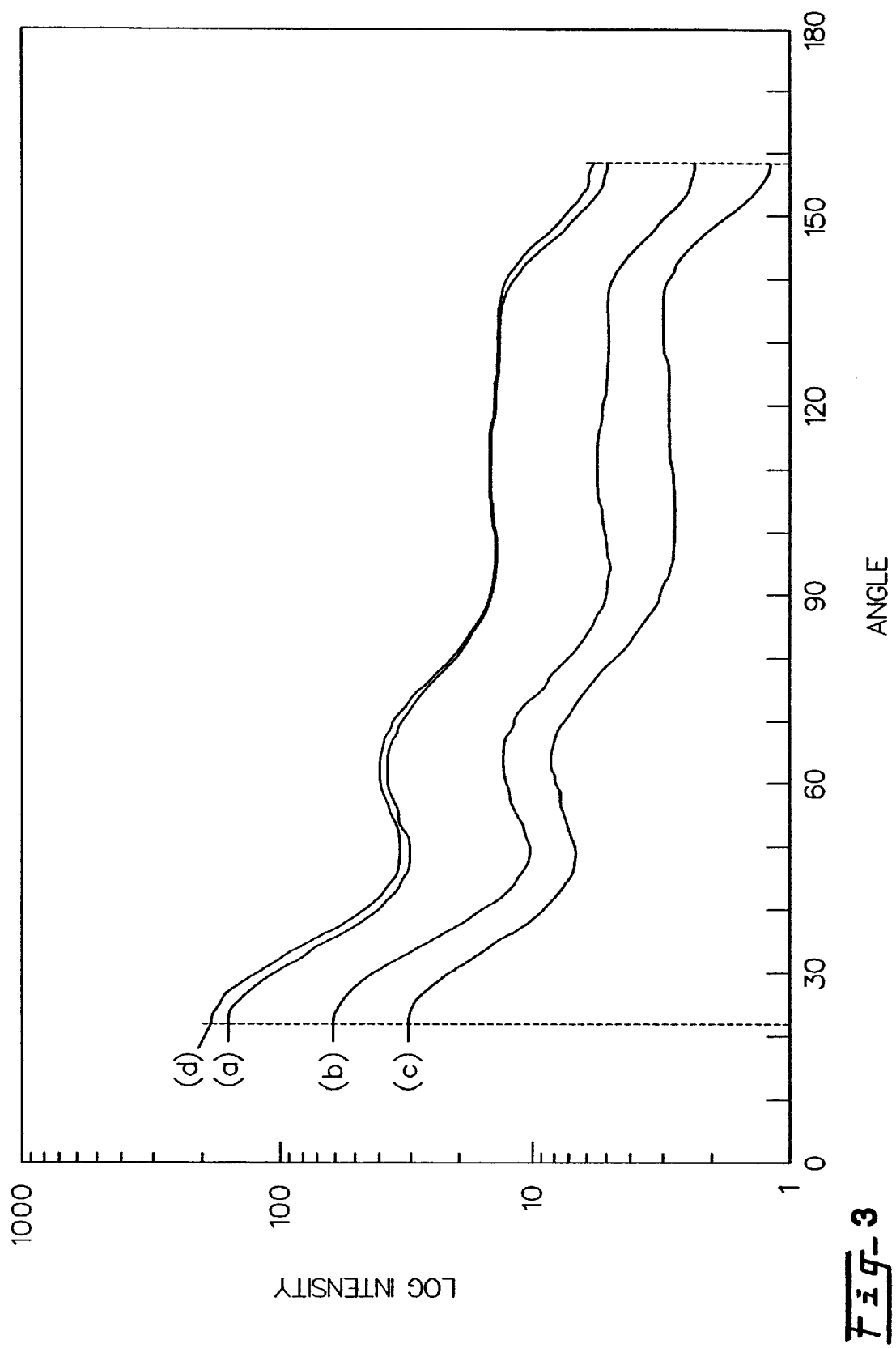

FIG. 3 is a MALS graph showing the antimicrobial effects of:
  (a) a sixty-minute treatment with 2 ppm tetrasilver tetroxide;
  (b) a twenty-minute treatment with 0.3 ppm ozone; and
  (c) a twenty-minute treatment with 0.3 ppm ozone and 2 ppm tetrasilver tetroxide. The tetrasilver tetroxide alone (a) was little more effective than the untreated control (d). Twenty minutes of ozone alone (b) produced a significant killing effect, but the combination of ozone and tetrasilver tetroxide (c) was much more potent than either compound alone.

Without wishing to be bound by any theories, it appears that in addition to acting as a killing agent in its own right, ozone is surprisingly able to activate the antimicrobial activity of tetrasilver tetroxide, thus yielding a synergistic killing effect exceeding the individual killing effects of either non-activated tetrasilver tetroxide or ozone.

EXAMPLE 5

Ozone Stability Testing 6.1 mg/L (6.1 ppm) of ozone was provided in deionized, distilled water over a 15 minute period. The solution was allowed to stand with stirring by a magnetic stirrer over a 24-hour period, taking periodic readings of the ozone concentration. By 2 hours, the ozone concentration was 3 ppm and progressively dropped to 0.01 ppm by 18 hours. This represented a half-life of approximately 2 hours. When 2 ppm tetrasilver tetroxide was added, the rate of decay was unexpectedly lengthened, such that 0.12 ppm of ozone was present after 18 hours (approximately an order of magnitude higher than would have been expected in the absence of tetrasilver tetroxide) and by 24 hours, 0.03 ppm of ozone oxidizing activity was still present.

Further research showed that neither tetrasilver tetroxide alone nor chemically-activated tetrasilver tetroxide (i.e., activated with potassium monopersulfate as described in the Comparative Examples) gave measurable oxidation as measured by the indigo dye method. Thus, the reduced half-life of ozone in the presence of tetrasilver tetroxide does not appear to be merely an additive effect or an experimental flaw arising from the use of the indigo dye method, but rather appears to be a surprising synergistic effect.

While the invention has been described in detail and with reference to specific examples thereof, it will be apparent to one skilled in the art that various changes and modifications can be made therein without departing from the spirit and scope thereof.

What is claimed is:
1. Ozonated tetrasilver tetroxide.
2. The ozonated tetrasilver tetroxide of claim 1, having an antimicrobial effect greater than a reference antimicrobial effect of non-activated tetrasilver tetroxide.
3. The ozonated tetrasilver tetroxide of claim 1, having an antimicrobial effect at least equal to a reference antimicrobial effect of potassium monopersulfate-activated tetrasilver tetroxide.
4. The ozonated tetrasilver tetroxide of claim 1, prepared by a process comprising providing tetrasilver tetroxide and ozone in a fluid medium.
5. The ozonated tetrasilver tetroxide of claim 4, wherein said fluid medium is water.
6. The ozonated tetrasilver tetroxide of claim 5, wherein an initial ratio of said ozone to said tetrasilver tetroxide provided in said fluid water is 1:10 to 10:1.
7. The ozonated tetrasilver tetroxide of claim 6, wherein an amount of said ozone provided in said fluid medium is from 0.5 to 7.0 ppm and a concentration of said tetrasilver tetroxide provided in said fluid water is from 0.5 to 7.0 ppm.
8. A composition comprising water and the ozonated tetrasilver tetroxide of claim 1.
9. The composition of claim 8, further comprising ozone.
10. The composition of claim 9, wherein said ozonated tetrasilver tetroxide and said ozone are provided in amounts synergistically effective to kill pathogens.
11. The composition of claim 8, said composition being substantially devoid of ozone.
12. The composition of claim 8, said composition being substantially devoid of potassium monopersulfate.
13. The composition of claim 8, wherein said composition is a beverage prepared by a process comprising providing tetrasilver tetroxide and ozone in a fluid medium in antimicrobially effective amounts suitable for human consumption.
14. The composition of claim 8, wherein said composition is a disinfectant prepared by a process comprising providing tetrasilver tetroxide and ozone in a fluid medium in antimicrobially effective amounts unsuitable for human consumption.
15. The composition of claim 8, wherein said composition is packaged in a container and labeled as a cleaning product.
16. A water disinfection method, comprising providing the ozonated tetrasilver tetroxide of claim 1 in water.
17. The method of claim 16, wherein said ozonated tetrasilver tetroxide is provided in said water in an amount of about 0.5 to 7 ppm.
18. The method of claim 16, wherein said ozonated tetrasilver tetroxide is provided in said water by combining tetrasilver tetroxide and ozone in said water.
19. The method of claim 18, wherein an initial ratio of said ozone to said tetrasilver tetroxide provided in said fluid water is 1:10 to 10:1.

20. The method of claim 19, wherein an amount of said ozone provided in said fluid water is from 0.5 to 7.0 ppm and a concentration of said tetrasilver tetroxide provided in said fluid water is from 0.5 to 7.0 ppm.

21. A method for increasing a half-life of ozone in water, said method comprising providing tetrasilver tetroxide in said water along with said ozone.

* * * * *